United States Patent [19]
O'Brien

[11] Patent Number: 5,771,901
[45] Date of Patent: Jun. 30, 1998

[54] ERGONOMIC PALMAR SUPPORT

[76] Inventor: Virginia H. O'Brien, 1141 Hillcrest Dr., Woodbury, Minn. 55125

[21] Appl. No.: 789,091

[22] Filed: Jan. 27, 1997

[51] Int. Cl.[6] .................................................. A61F 5/37
[52] U.S. Cl. ............................ 128/878; 128/879; 602/21
[58] Field of Search .................................. 128/845, 846, 128/877, 878, 879, 882; 602/20, 21; 2/16, 21

[56] References Cited

U.S. PATENT DOCUMENTS

| | | | |
|---|---|---|---|
| Re. 34,573 | 4/1994 | Calvert | 2/2 |
| 4,558,694 | 12/1985 | Barber | 128/87 |
| 4,617,684 | 10/1986 | Green et al. | 2/20 |
| 4,754,499 | 7/1988 | Pirie | 2/20 |
| 4,881,533 | 11/1989 | Teurlings | 128/878 |
| 5,031,640 | 7/1991 | Spitzer | 128/878 |
| 5,322,286 | 6/1994 | Frost | 273/165 |
| 5,330,249 | 7/1994 | Weber et al. | 297/214 |
| 5,339,465 | 8/1994 | Kyewski | 2/20 |
| 5,345,608 | 9/1994 | Mergens et al. | 2/16 |
| 5,350,418 | 9/1994 | Janevski | 602/21 |
| 5,413,553 | 5/1995 | Downes | 602/21 |
| 5,561,856 | 10/1996 | Pesco | 2/16 |

OTHER PUBLICATIONS

"Rehabilitation of the Hand: Surgery and Therapy", by James M. Hunter, M.D., Evelyn J. Mackin, P.T. and Anne D. Callahan, M.S., Fourth Edition, pp. 1825–1827 and 1836–1838.

Primary Examiner—Michael A. Brown
Attorney, Agent, or Firm—Westman, Champlin & Kelly, P.A.

[57] ABSTRACT

An arch support for a hand is a plate made to conform to the palm of the hand and has support edges The support bridges the palm between the thumb side and the little finger of ulnar side of the palm of the hand and extends from adjacent the distal wrist crease to the palmar crease. The support is molded to fit partially around the thumb and a portion of the heel of the hand. The support is held in place with a glove or with fasteners. When gripping an object such as a handle bar of a bicycle for example, the arch of the hand is supported to reduce ulnar and median nerve compression damage while the hand supports part of the upper body weight on the handle bars of a bicycle. The support is made of sufficiently rigid material so that it will distribute the loads supported on the handle bars across a wider surface of the palm of the hand, particularly by spanning the carpel tunnel and Guyon's canal to avoid damage to the median and ulnar nerves.

14 Claims, 5 Drawing Sheets

ERGONOMIC PALMAR SUPPORT

BACKGROUND OF THE INVENTION

The present invention relates to a molded, relatively rigid, support plate that covers the palm of a hand from distal to the distal wrist crease to just proximal to the palmar crease and extends laterally from the ulnar border of the hand to the base portion of the thumb and extending up into the web space to distribute outside compression forces over a large surface of the palm. The support plate decreases pressure specifically at the carpal tunnel and Guyon's canal.

In the prior art various pads have been utilized for reducing carpal tunnel syndrome, as well as for improving gripping on cylindrical objects such as baseball bats. For example, U.S. Pat. No. 5,031,640 shows a pad for reducing carpal tunnel syndrome, which occurs by compression of the median nerve. The pad or hand grip shown in patent '640 is placed between a tool and the hand, and provides a void area over the carpal tunnel. This device is essentially a grip that is similar to a bicycle hand grip with a recess in the portions overlying the median nerve. It is awkward to use, and relatively bulky. In one embodiment the use of a flexible pad in a glove is illustrated, but the bridging function of the present invention is not provided.

A hand accessory for swinging a bat, which comprises a molded grip of irregular shape that has a cylindrical receptacle and which can be gripped by a hand, is shown in U.S. Pat. No. 5,322,286. Other pads have been advanced for protecting the palm, but none which specifically adapt to the configuration of the hand and palm when used in connection with a bicycle handle bar and/or handle bar grip.

The reference book *Rehabilitation of the Hand: Surgery and Therapy*, Hunter et al. 4th edition (1995) pp. 1825–1827 provides a discussion of bicycling hand injuries, including handlebar palsy resulting from compression of the ulnar nerve in Guyon's canal. This is known as Guyon's canal syndrome. The injury was originally described as early as 1896. Treatment that is suggested to correct compression injuries includes frequently changing hand position, using gloves and padded handlebars, and correct bicycle fit. Otherwise, rest from the sport is recommended with use of a wrist splint to immobilize the hand. Several recent articles have discussed compression neuropathy as a problem for serious bikers, but the problem persists and is not solved by the presently recommended and common treatment of padded gloves or padded handle bars.

SUMMARY OF THE INVENTION

The present invention relates to a molded, relatively rigid hand support that extends across the palm of the hand. The support is preferably molded as a plate of substantially uniform thickness to conform generally to a partially cupped shape of the palm and extends from just distal to the distal wrist crease at its most proximal aspect, to just proximal to the distal palmar crease, thereby permitting the fingers to grip without interference. The lateral span of the support is from the hypothenar ridge at its most ulnar border, (that is it wraps partially around the edge of the palm on the little finger side) to the thumb side of the palm.

There is preferably a contoured molded saddle portion that supports the base of the thumb and extends to just beyond the metacarpophalangeal crease. The saddle is an integral extruded piece that wraps at least partially around the thumb and curves through the web space between the thumb and the index finger. The support plate is contoured for the open hand to conform to a surface such as a bicycle handle bar.

The hand support is preferably molded from a relatively rigid plastic, but it can be made of a formed metal or other rigid materials. The interior (palm facing) surface of the hand support can be thinly padded to provide comfort if desired, or the surface of the hand support can contact the skin directly.

The rigidity of the hand support provides a bridge to decrease the localized compression pressure across the carpal tunnel and Guyon's canal where the median and ulnar nerves course, respectively. The saddle for the base portion of thumb is premolded in a partially gripped position, and the hand support plate terminates without covering the distal palmar crease, so that the fingers can be flexed and tightened onto a handle bar grip while the base portion of the palm and the thumb are well supported.

The hand support can be worn separately and merely strapped in place on a hand or held in any desired way, or inserted into a glove, such as a biking glove. The hand support can be incorporated into the palm section of a glove as well.

The hand support provides comfort by distributing the weight normally exerted on the handle bars of a bike, in particular, across a wider area to reduce localized pressures.

DETAILED DESCRIPTION OF THE PREFERRED EMBODIMENTS

Figure 1:
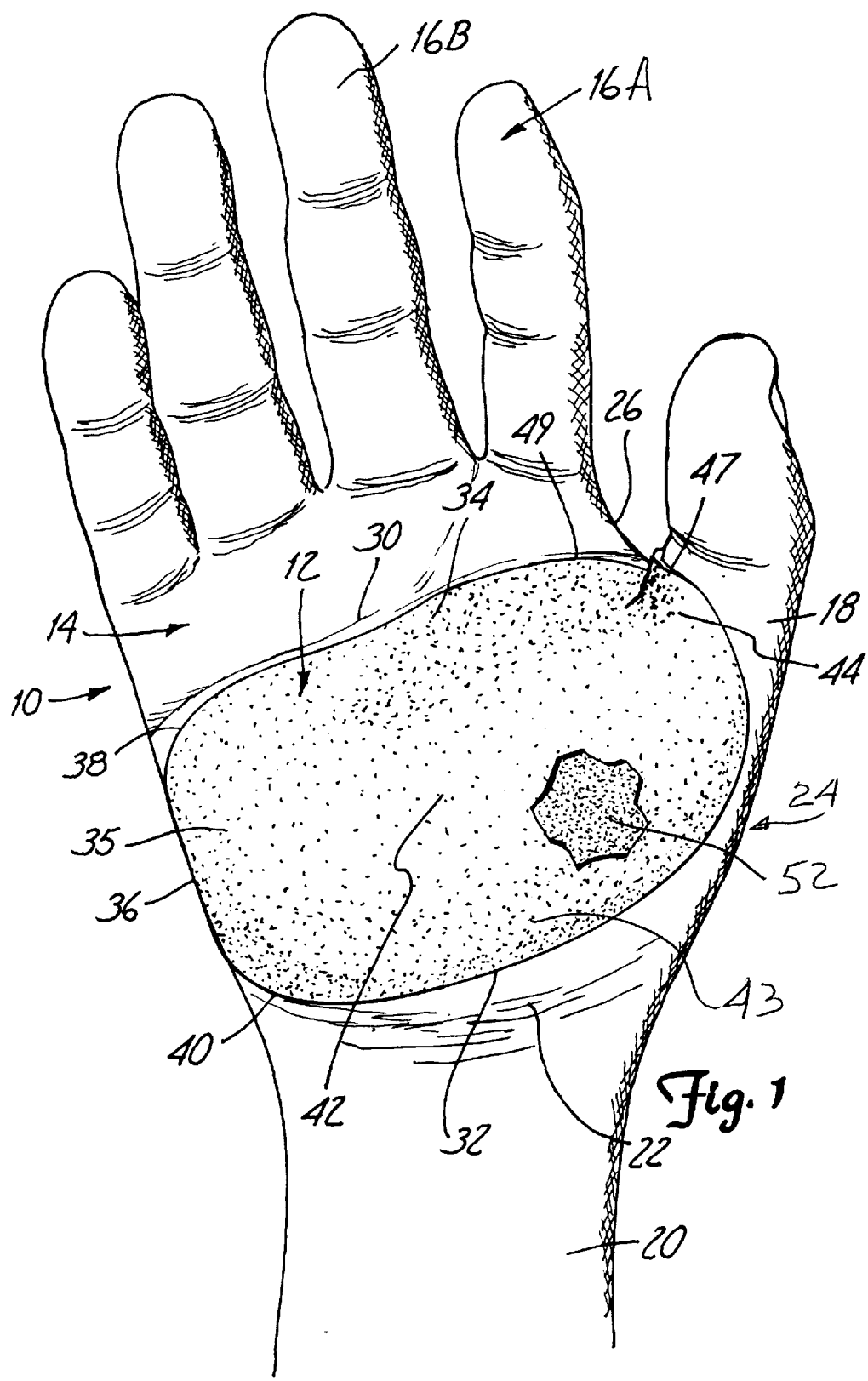
FIG. 1 is a perspective view of a hand showing a hand support made according to the present invention placed thereon.

As shown in FIG. 1, a hand 10 is supported on a hand support 12 made according to the present invention. The hand 10 of a user or wearer includes a palm portion 14, fingers 16, and a thumb 18. A wrist portion 20 supports the hand 10, which hinges along a distal wrist crease indicated generally at 22. The thumb 18 has a base joint or knuckle in the region indicated at 24, and a skin web 26 joins the thumb 18 to the hand just to the proximal side of the index finger 16A.

The palm 14 also has a distal palmar crease 30 in the region proximal to the first finger joints. The palmar crease 30 does not span across the entire palm in an unbroken line in many people, but curves up between the index finger 16A and the adjacent middle finger 16B, and separately curves in from the skin web 26 down toward the center of the palm 14. It is the fold line formed when the flexing of the fingers 16 relative to the base joint 24 of the thumb.

Figure 5:
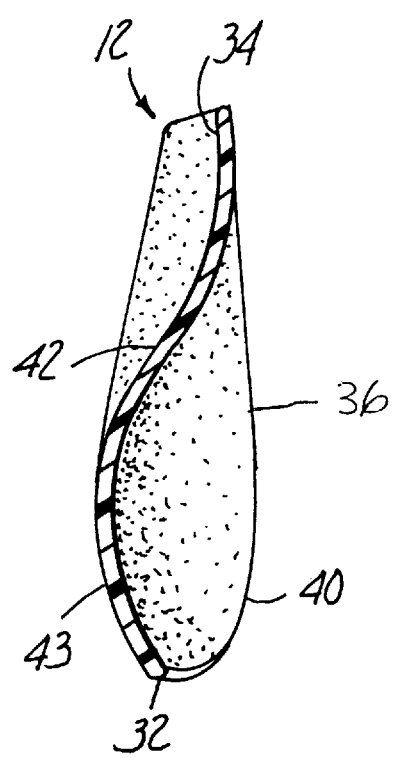
FIG. 5 is a sectional view taken along line 5–5 in FIG. 3.
Figure 6:
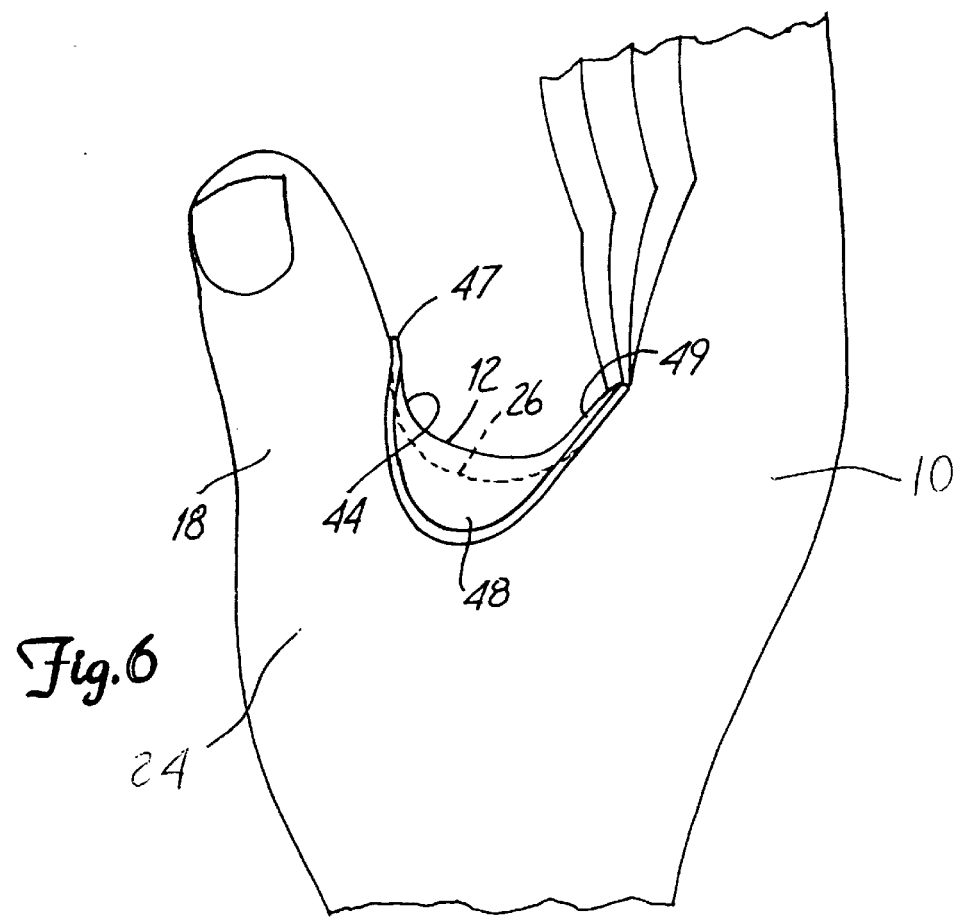
FIG. 6 is a fragmentary perspective of the hand support on a hand as viewed from the thumb side.

The hand support 12 is substantially uniform thickness, has an irregularly shaped periphery, and has a curved edge portion 32 that extends over the base of the palm adjacent and just distal to the distal wrist crease 22, up to an edge 34 proximal to the distal palmar crease 30. The palmar crease edge 34 of the hand support lies laterally across the palm as can be seen, from the little finger or ulnar side of the palm at 35, and curves down as at 36 to wrap around the hypothenar ridge on its most ulnar border up to the edge adjacent the palmar crease 30. The curved portion 36 is a partial hook that actually wraps partially around the ulnar or little finger side of the hand. The hand support 12 has rounded corners such as those shown at 38 and 40 on the ulnar side of the hand support. The mid portions 42 of the hand support curves concave slightly relative to edge portions 43, 34 and 35 to generally conform to a very shallow cup shape of the palm that is formed when the thumb 18 is partially bent as shown in FIG. 1. The concavity of mid portion 42 is illustrated in FIG. 5.

The hand support 12 is formed around the fleshy base of the thumb in the region 43, and the edge portion 32 thus is formed downwardly on the distal wrist crease side of region 43.

The thumb 18 is supported on a thumb saddle portion 44 of the hand support that smoothly joins edge portions 32 along a curved edge 45. The thumb saddle curves upwardly from the base of the thumb 18, and terminates at an edge 47 between the first and second joints of the thumb 18. The thumb saddle 44 only partially encircles the thumb and is open to the outside so the hand support can easily be applied. The hand support curves so that the thumb is partially in a gripping motion when engaging the thumb saddle 44. The edge portion 48 overlaps and extends around the skin web 26 slightly and then curves back to join the edge 34 as shown at 49. The edge portion 48 hooks or seats over the edge of the skin web portion 26 to seat the hand support 12 properly.

The thumb saddle provides a radial border for proper fit of the palm in the support. The edge portion 35 just inwardly of curved edge portion 36 on the ulnar side of the palm also provides for a distinct support region. The base 32 and the palmar crease edge 34 also support the hand support so the center portion 42 and the portions 35 overlying Guyon's canal for the ulnar nerve and the carpel tunnel form a compression carrying bridge to reduce concentrated compression loads on these sensitive regions.

The hand support 12 is preferably made of a relatively rigid material, although when made of plastic it is still somewhat flexible. The hand support 12 is capable of supporting the weight that would be placed on the handle bars during riding without substantial flexing. The supported weight thus will be distributed across a wider surface area of the hand and palm by the use of the relatively rigid hand support of the present invention.

Figure 2:
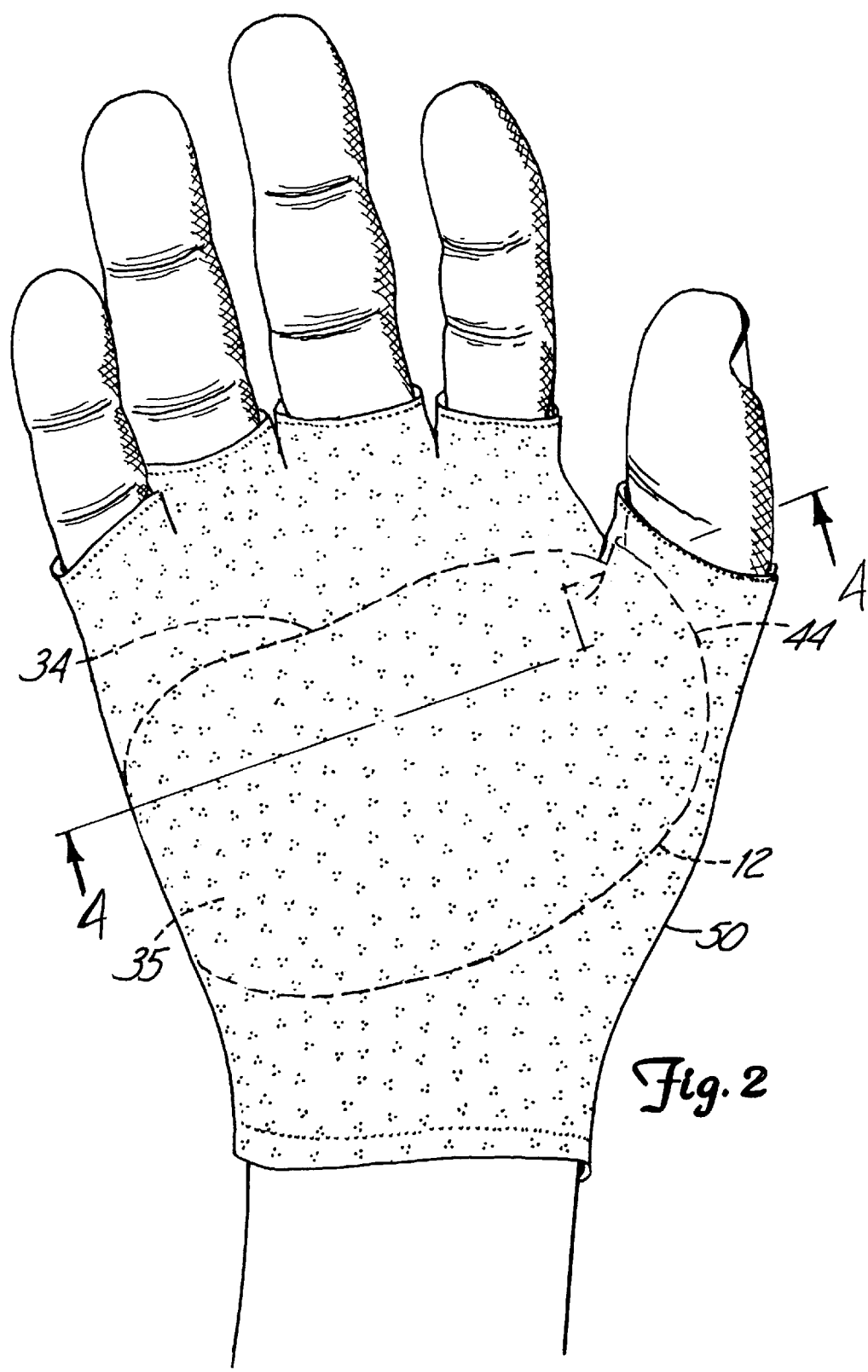
FIG. 2 is a view similar to FIG. 1, but showing the hand having a glove covering the hand support.
Figure 3:
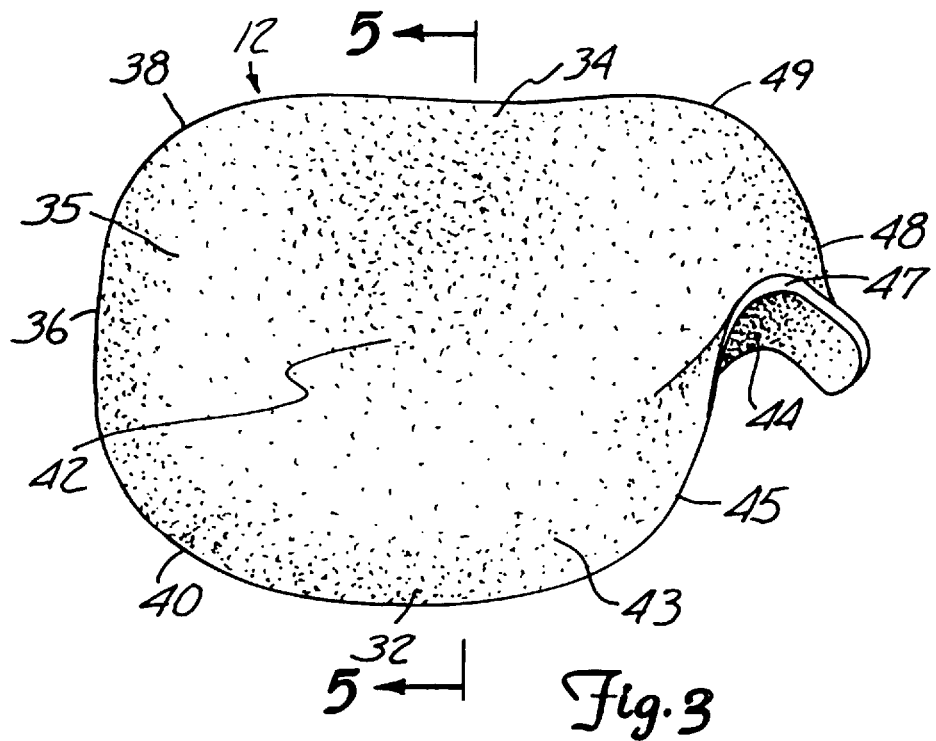
FIG. 3 is a perspective view of the hand support of FIG. 1.
Figure 4:
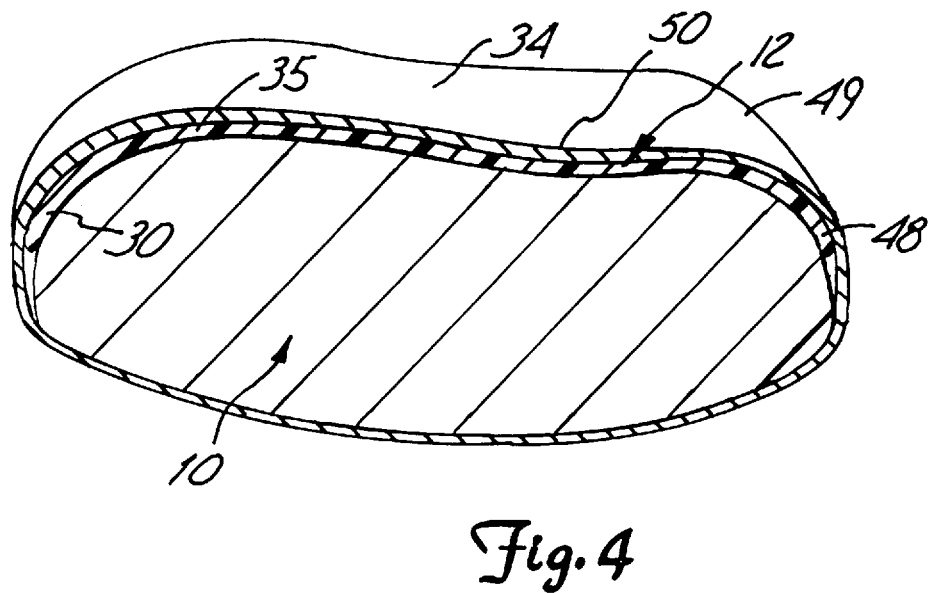
FIG. 4 is a sectional view taken generally on line 4—4 in FIG. 1.

The hand support 12 is outlined in FIG. 2 in dotted lines and is placed on the interior of a biker's glove 50. The shape of the hand support permits the fingers and thumb to be operated for gripping a handle bar of a bike without interfering with folding or the creasing of the palm when the fingers are flexed in a grip, but support across the span or lateral dimension of the palm is provided. As shown in FIG. 4, there is support for the regions over Guyon's canal, as well as over the carpal tunnel.

As shown in FIG. 4, where the hand support is broken away, a foam lining indicated at 52 can be provided on the skin side of the hand support to provide for conformability to aid in distributing the localized pressures across a wider surface area.

Figure 7:
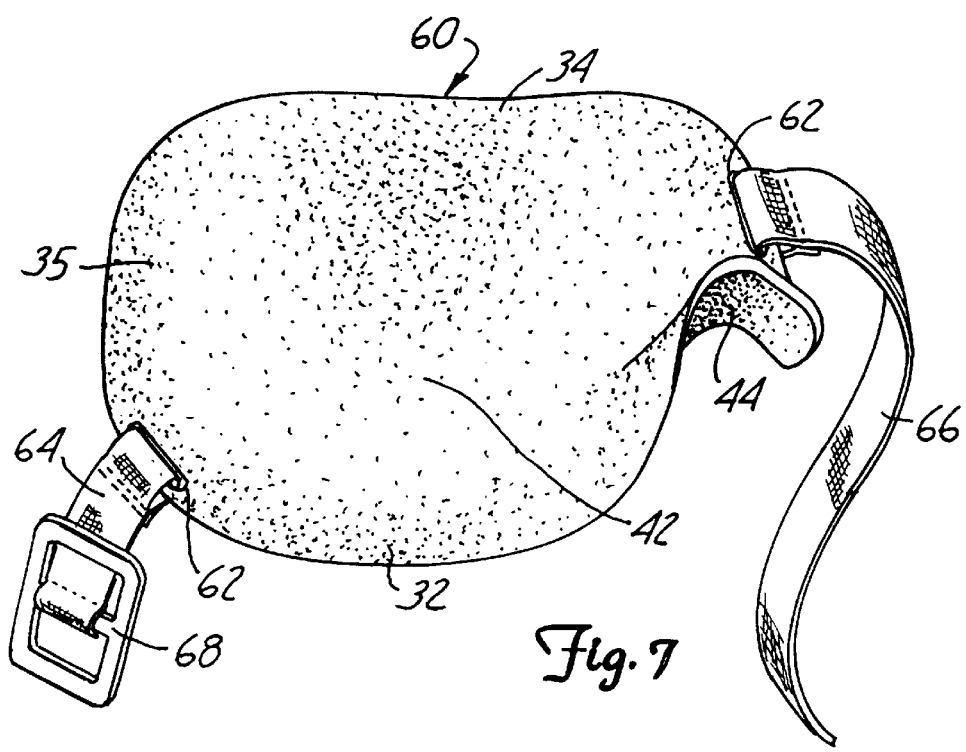
FIG. 7 is a perspective view of a modified form of the invention illustrating a fastener strap for holding the hand support in position.

FIG. 7 shows a modified version of the hand support 60 with the thumb saddle 44 and other components numbered as previously shown, but including strap receiving slots 62 at desired locations. Ends of strap sections 64 and 66 are retained in the slots 62. The opposite ends of the strap section can be buckled together with a suitable buckle 68 for fastening the hand support onto the hand for use. Velcro fastener can be used, or a continuous elastic band also will work.

The curving or wrapping of the hand support edge around the skin web 26 between the thumb and the index finger will insure that the hand support is properly positioned to provide distribution of pressure and reducing localized pressure on nerves in the carpal tunnel and Guyon's canal.

Again, the hand support of the present invention is to support the hand arches and distribute the weight supported by the hands over a larger surface area, thus decreasing the pressure specifically at the two most vulnerable areas of the palm, the carpal tunnel and Guyon's canal, where the median and ulnar nerves course, respectively. The hand support can be worn separately as shown in FIG. 7, or inserted into a glove as shown in FIG. 2, or in any other desired way it can be held in place during use.

While the primary use envisioned is in connection with bicycle handlebars where weight is carried on the hands for long periods of time, particularly in distance cycling, the hand support can be used in other places where weight is carried across the palm on a relatively small diameter cylinder or other object.

The preferred material is a moldable plastic. A selected semi-rigid to rigid plastic material about ⅛ of an inch thick and molded as shown operates satisfactorily.

Although the present invention has been described with reference to preferred embodiments, workers skilled in the art will recognize that changes may be made in form and detail without departing from the spirit and scope of the invention.

What is claimed is:

1. A hand support comprising a unitary member that extends across and is contiguous with the palm portion of a hand of a wearer, said hand support being made of a material that is sufficiently rigid to distribute weight across a surface area of the palm when subjected to loads in localized regions, and comprising a first edge portion extending just distal to the distal wrist crease, and curved upwardly from the first edge, the hand support having a second edge portion joining the first edge portion and extending in direction to overlie an ulnar side of the hand of a wearer, the hand support having a third edge portion opposite from the first edge portion, the third edge portion terminating on a proximal side of a distal palmar crease of the hand of a wearer, and a thumb saddle formed on an opposite side from the second edge portion contoured to receive and support a thumb of a user, and extending no farther than the second joint of the thumb to permit the outer end of the thumb to flex, the edge portions and thumb saddle providing load support regions for the hand support while permitting the hand to bend at the palmar crease.

2. The hand support of claim 1, wherein the junction between the second edge portion and the third edge portion forms a rounded corner.

3. The hand support of claim 1, wherein the hand support has a thumb side portion adjacent the thumb saddle that curves to fit over a web between a thumb and an index finger of a hand of a wearer, the thumb side portion smoothly joining the thumb saddle and a fourth edge portion.

4. The hand support of claim 1 and a foam lining on a surface of the hand support on an interior thereof.

5. The hand support of claim 1 used in combination with a glove, said glove covering the hand support in place when placed on a hand of a wearer.

6. The hand support of claim 1, and a strap connected to opposite edges of the hand support operable to encircle the hand of a wearer of the hand support.

7. The hand support of claim 1, wherein the hand support has center portions between the edge portions which are concave relative to the edge portions.

8. The hand support of claim 1, wherein the second edge portion curves to form a shallow hook on an inner side of the hand support.

9. A hand support for use when gripping an object, comprising a plate member that extends across and is contiguous with a palm portion of a hand of a wearer, said hand support being made of a material that is sufficiently rigid to distribute weight across a surface area of the palm portion when subjected to loads in localized regions, and comprising a first laterally extending edge portion extending from adjacent and distal of a distal wrist crease of a wearer to a second laterally extending edge proximal to a palmar crease of the hand of a wearer across the entire palm portion, and the hand support having a third edge portion joining the first and second edge portions and extending along an ulnar side of the hand of a wearer to support the palm at such third edge portion, and having a thumb saddle on a fourth edge portion and opposite from the third edge portion contoured to receive and support a thumb of a wearer when the thumb is partially closed and a load is supported by the hand support, wherein the thumb saddle terminates beyond and adjacent to the first joint of the thumb.

10. The hand support of claim 9, wherein the fourth edge portion curves over a web between the thumb and an index finger of the hand of a wearer, and smoothly joins the thumb saddle.

11. The hand support of claim 9, wherein both the third edge portion and fourth edge portion partially curve in a direction to partially surround underlying sides of the hand of a wearer to provide support for such hand on the third and fourth edge portions.

12. The hand support of claim 11, wherein the first edge portion carries in the same direction as the third and fourth edge portions to provide three edge portions tending to seat the hand of a wearer therebetween.

13. The hand support of claim 12 wherein the plate member is molded as a unitary member.

14. The hand support of claim 11, wherein the thumb saddle curves to form a partial cylinder open on a side of the thumb saddle facing outwardly from the plate member.

* * * * *